United States Patent [19]

Nakao et al.

[11] 4,126,745

[45] Nov. 21, 1978

[54] 7-METHOXYCEPHALOSPORIN DERIVATIVES

[75] Inventors: Hideo Nakao; Hiroaki Yanagisawa; Bunji Shimizu; Masakatsu Kaneko; Mitsuo Nagano; Shinichi Sugawara, all of Hiromachi, Japan

[73] Assignee: Sankyo Company Limited, Tokyo, Japan

[21] Appl. No.: 676,488

[22] Filed: Apr. 13, 1976

[30] Foreign Application Priority Data

Apr. 30, 1975 [JP] Japan .................................. 50-52180
May 7, 1975 [JP] Japan .................................. 50-55026

[51] Int. Cl.$^2$ .................. C07D 501/50; C07D 501/36; A61K 31/545
[52] U.S. Cl. ........................................ 544/21; 544/4; 424/246; 424/245
[58] Field of Search ................. 260/243 C; 544/21, 4

[56] References Cited

U.S. PATENT DOCUMENTS

| | | | |
|---|---|---|---|
| 3,516,997 | 6/1970 | Takano et al. | 260/243 C |
| 3,898,221 | 8/1975 | DeMarinis et al. | 260/243 C |
| 3,920,639 | 11/1975 | Dolfini | 260/243 C |
| 3,971,779 | 7/1976 | Nudelman | 260/243 C |
| 4,059,578 | 11/1977 | DeMarinis et al. | 544/21 |

FOREIGN PATENT DOCUMENTS 832,797 2/1976 Belgium.
2,455,884 5/1975 Fed. Rep. of Germany.
2,539,411 4/1976 Fed. Rep. of Germany.

OTHER PUBLICATIONS

Lewis, Antimicrobial Agents & Chemotherapy-1968, pp. 109-114 (1969).

Primary Examiner—Donald G. Daus
Assistant Examiner—Diana G. Rivers
Attorney, Agent, or Firm—Flynn & Frishauf

[57] ABSTRACT

A compound having the formula

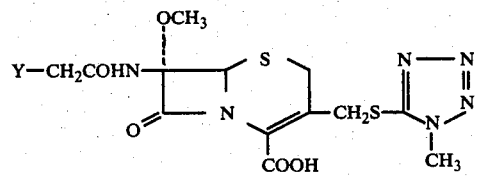

wherein Y represents a 2-carboxyethylthio group or a trifluoromethylthio group and a nontoxic pharmaceutically acceptable salt thereof are useful as antibacterial agents. They may be prepared by (a) reacting a compound having the formula

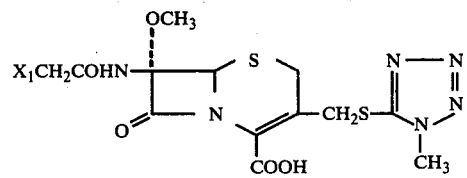

wherein $X_1$ represents a halogen atom with a compound having the formula $$Y - H$$

wherein Y has the same meaning as defined above, or (b) reacting a compound having the formula

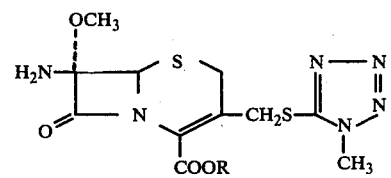

wherein R represents a protective group for the carboxyl group with a compound having the formula $$Y - CH_2COX_2$$

wherein $X_2$ represents a halogen atom and Y has the same meaning as defined above and removing the protective group for the carboxyl group from the resulting product, or (c) reacting a compound having the formula

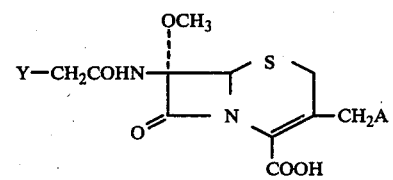

wherein A represents an acetoxy group or a carbamoyloxy group and Y has the same meaning as defined above with 5-mercapto-1-methyl-1H-tetrazole or its alkali metal salt.

3 Claims, No Drawings

7-METHOXYCEPHALOSPORIN DERIVATIVES

This invention relates to novel 7α-methoxycephalosporin derivatives of value as antibacterial agents, as nutritional supplements in animal feeds and as therapeutic agents in poultry and animals, including man, in the treatment of infections diseases caused by Gram-positive and Gram-negative bacteria.

Certain 7α-methoxycephalosporin derivatives have been disclosed in Japanese Patent Provisional Publication Nos. 3286/71 and 931/72, the Journal of the American Chemical Society, vol. 94, p. 1408 (1972), ibid, vol. 94, p. 1410 (1972) and ibid, vol. 95, p. 2401 (1973).

None of the compounds cited therein, however, have been put into practice because they have not antibacterial action to a satisfactory extent against both Gram-positive and Gram-negative bacteria.

It is thus an object of the present invention to provide a new class of 7α-methoxycephalosporin derivatives which have excellent antibacterial activity. It is another object of this invention to provide processes for the preparation of such 7α-methoxycephalosporin derivatives.

In accordance with the present invention, there are provided 7αl-methoxycephalosporin derivatives having the formula

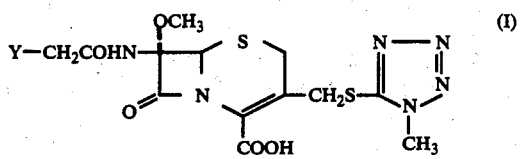

wherein Y represents a 2-carboxyethylthio group or a trifluoromethylthio group and the nontoxic pharmaceutically acceptable salts thereof, including their alkali or alkaline earth metal salts, e.g., the sodium, potassium, calcium or aluminum salts, the ammonium salts and the substituted ammonium salts, e.g., the triethylammonium, dicyclohexylammonium, dibenzylammonium or N-ethylpiperidinium salts.

The present invention also provides a process for the preparation of 7α-methoxycephalosporin derivatives having the formula (I) and nontoxic pharmaceutically acceptable salts thereof which comprises (a) reacting a compound having the formula

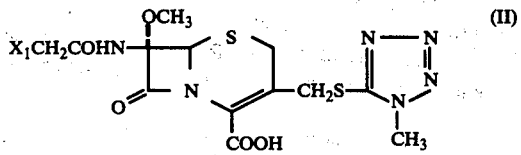

wherein $X_1$ represents a halogen atom with a compound having the formula $$Y — H \quad \text{(III)}$$

wherein Y has the same meaning as defined above, or (b) reacting a compound having the formula

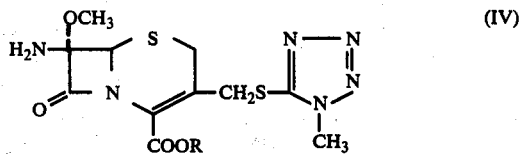

wherein R represents a protective group for the carboxyl group having the formula $$Y — CH_2COX_2 \quad \text{(V)}$$

wherein $X_2$ represents a halogen atom and Y has the same meaning as defined above and removing the protective group for the carboxyl group from the resulting product, or (c) reacting a compound having the formula

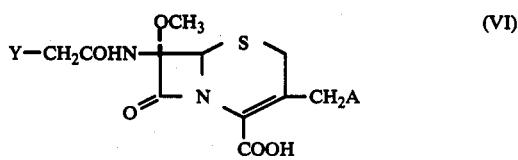

wherein A represents an acetoxy group or a carbamoyloxy group and Y has the same meaning as defined above with 5-mercapto-1-methyl-1H-tetrazole or its alkali metal salt.

In the above formulae, $X_1$ and $X_2$ are preferably bromine or chlorine. R is preferably a protective group for a carboxyl group which may be eliminated by treatment with an acid.

Representative examples of such a protective group include a methyl group substituted with a phenyl radical with or without substitutents on the aromatic ring, e.g., benzhydryl, p-methoxybenzyl; a tertiary lower alkyl group, e.g., tert-butyl, tert-amyl; an alkoxymethyl group, e.g., benzyloxymethyl, methoxymethyl; an alkali metal, e.g., potassium, sodium, an amine, e.g., diisopropylamine, dicyclohexylamine, triethylamine, pyridine; and a quarternary ammonium, e.g., trimethylbenzylammonium.

The method (a) of this invention can be carried out by treating the compound (II) with the compound (III) usually in the presence of an appropriate inert solvent. As to the solvent, there is no particular limitation so far as it does not participate in the reaction. As preferable solvents are mentioned dimethylsulfoxide, dimethylformamide, acetone, water and the like, but dimethylformamide is most preferably used. The presence of a base accelerates the reaction. Representative examples of such a base include alkali metal hydrogen carbonates, e.g., sodium or potassium hydrogen carbonate, alkali metal carbonates, e.g., sodium or potassium carbonates, tertiary amines, e.g., triethylamine, dimethylaniline, diethylaniline, pyridine. The reaction is preferably carried out at room temperature or under ice-cooling.

The desired product (I) thus prepared can be recovered by a conventional method from the reaction mixture. For example, the reaction mixture is diluted with water, extracted with ethyl acetate at pH 2 and the solvent is removed from the extract to give the desired product which, if necessary, is purified by chromatography.

A 7β-Haloacetamido-7α-methoxycephalosporin derivative having the above-described formula (II), which is employed in the method (a) as a starting material can be prepared by the following sequence of reactions: The known 7-amino-3-(1-methyl-1H-tetrazol-5-yl)thiomethyl-3-cephem-4-carboxylic acid ester is condensed with 4-hydroxy-3,5-di-tert-butylbenzaldehyde and the product is oxidized and subsequently reacted with methanol affording 7β-(4-hydroxy-3,5-di-tert-butylbenzylideneamino)-7α-methoxy-3-(1-methyl-1H-tetrazol-5-yl)thiomethyl-3-cephem-4-carboxylic acid ester, from which the benzylidene group is eliminated to yield 7β-amino-7α-methoxy-3-(1-methyl-1H-tetrazol-5-yl)thiomethyl-3-cephem-4-carboxylic acid ester (IV). The 7-amino compound thus prepared is then reacted with a halogenoacetic acid halide and the product is finally saponified.

The first step in the method (b) of this invention can be preferably carried out by reacting the compound (IV) with the compound (V) in the presence of an acid binding agent at or below room temperature, usually in an appropriate inert solvent, for example, dichloroethane, chloroform, methylene chloride, acetone, tetrahydrofuran and the like. As the acid binding agent, there may be used such a base as mentioned in method (a).

The starting material employed in the process of the present invention, 7β-amino-7α-methoxy-3-(1-methyl-1H-tetrazol-5-yl)thiomethyl-3-cephem-4-carboxylic acid in which the carboxyl group at the 4-position is protected or forms a salt, as represented by the above-described formula (IV), can be prepared, for instance, according to the procedure described in Example 5 and others in Japanese Patent Provisional Publication, No. 931/72, by reducing 7-azido-7-methoxy-3-(1-methyl-1H-tetrazol-5-yl)thiomethyl-3-cephem-4-carboxylic acid ester or a salt in the presence of platinum oxide in an atmosphere of hydrogen; or by condensing a benzhydryl ester prepared from the known 7-amino-3-(1-methyl-1H-tetrazol-5-yl)thiomethyl-3-cephem-4-carboxylic acid with 4-hydroxy-3,5-di-tert-butylbenzaldehyde, followed by oxidation and subsequent treatment with methanol of the product affording 7β-(4-hydroxy-3,5-di-tert-butylbenzylideneamino)-7α-methoxy-3-(1-methyl-1H-tetrazol-5-yl)thiomethyl-3-cephem-4-carboxylic acid benzhydryl ester, from which the benzylidene group is finally eliminated. A protecting group other than the above-described benzhydryl group and a salt as well as may be used in the above sequence of reactions.

In case where the carboxyl halide having the formula (V) in which Y is 2-carboxylethylthio group is employed, it is desirable to protect the carboxyl group with a diphenylmethyl group.

A 7β-Acylamino-7α-methoxycephalosporin derivative thus prepared can be recovered by a usual manner from the reaction mixture. For instance, the reaction mixture is washed with water, the solvent removed from the mixture and, if desired, the product is purified by a column chromatography.

The product thus obtained can be converted into the desired compounds having the general formula (I) by eliminating the protecting group for the carboxylic acid by a usual manner. The elimination reaction of the protecting group can be carried out by treating the product with an acid. The acid treatment can be performed by contacting the product with trifluoroacetic acid or an acid with a similar acidity in the presence or absence of a suitable solvent. The acid may be employed without any particular limitation, but trifluoroacetic acid is preferably used. As to the solvent which may be employed in this reaction, there is no critical limitation so far as it does not participate in the reaction. As examples of such solvents may be mentioned a halogenated hydrocarbon such as chloroform, dichloromethane and the like, and a substituted or unsubstituted aromatic hydrocarbon such as benzene, toluene, chlorobenzene, anisole and the like. Usually anisole is preferable. The reaction temperature is not particularly critical, but the reaction is carried out at relatively low temperature usually between 0° C. and 30° C. in order to obtain the desired product in good yield. The reaction time may be varied mainly depending upon the kind of the protecting group, acid, solvent and reaction temperature which are employed in the reaction, but it usually takes about several tens minutes. After the reaction is completed, the end product having the general formula (I) thus formed can be recovered by a usual manner from the reaction mixture. For instance, the reaction mixture is extracted with an aqueous solution of a weak base such as, for example, dipotassium hydrogen phosphate, the extract is made acidic and extracted again with a suitable solvent, and the solvent is removed from the extract to leave the desired product.

The method (c) may be preferably carried out by reacting the compound (VI) with 5-mercapto-1-methyl-1H-tetrazole in the presence of an alkaline substance and an appropriate inert solvent, preferably water. As the alkaline substance, there may be preferably used an alkali metal hydroxide, e.g., potassium hydroxide and sodium hydroxide, an alkali metal hydrogen carbonate, e.g., potassium hydrogen carbonate and sodium hydrogen carbonate, or ammonia.

The reaction is conducted at or above room temperature. The compounds (VI) are novel and may be prepared by reacting the compound having the formula

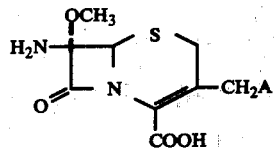

wherein A has the same meaning as defined above with the compound having the formula

wherein $X_3$ is a halogen atom.

The compounds of the formula (I) which are prepared by the above-described process may be converted to nontoxic pharmaceutically acceptable salts thereof by a conventional neutralization procedure.

The compounds of this invention have useful antibacterial properties. In particular, they show in vitro and in vivo activity against Gram-positive and Gram-negative bacteria and are accordingly valuable as antibacterial agents.

Minimum inhibitory concentrations (MIC) were determined for the compounds of this invention. The results are reported in Table 1.

Table

| Compounds | I A | I B | II A | II B | III | IV | V A | V B | VI | VII |
|---|---|---|---|---|---|---|---|---|---|---|
| 7β-(2-Carboxyethylthioacetamido)-7α-methoxy-3-(1-methyl-1H-tetrazol-5-yl)thiomethyl-3-cephem-4-carboxylic Acid | 6.2 | 12.5 | 0.8 | 0.8 | 0.4 | >200 | 0.4 | 50 | 0.8 | 0.2 |
| 7α-Methoxy-7β-trifluoromethylthioacetamido-3-(1-methyl-1H-tetrazol-5-yl)thiomethyl-3-cephem-4-carboxylic Acid | 0.2 | 0.4 | 1.5 | 3.1 | 0.8 | >200 | 1.5 | 50 | 6.2 | 0.4 |
| Cefoxitin | 0.8 | 1.5 | 3.1 | 3.1 | 3.1 | >200 | 3.1 | >200 | 3.1 | 1.5 |

Minimum inhibitory concentration: mcg./ml
IA: *Staphylococcus aureus* 209 P
IB: *Staphylococcus aureus* (resistant to CP and PC)
IIA: *Escherichia coli* NIHJ
IIB: *Escherichia coli* 609 (resistant to CER)
III: *Shigella flexneri* 2a
IV: *Pseudomonas aeruginosa*
VA: *Klebsiella neumoniae* 806
VB: *Klebsiella neumoniae* 846 (resistant to CER)
VI: *Proteus vulgaris*
VII: *Salmonella enteritidis Gaertner*

As shown above, the compounds which are prepared according to the process of the present invention exhibit excellent antibacterial activities against broad pathogenic microorganisms.

These compounds can be administered orally or parenterally, for instance, in the form of a capsule, tablet or injection, but the injection is usually preferable. The dosage unit may be varied depending upon the age, symptoms, body weight and the like of the patient, but a usual unit is in amounts of from 250mg to 300mg per day for adults, and it is administered separately three or four times a day. But, if desired, more than the above amount may be used.

The following examples are given for further illustration of the present invention.

EXAMPLE 1

7β-(2-Carboxyethylthioacetamido)-7α-methoxy-3-(1-methyl-1H-tetrazol-5-yl)thiomethyl-3-cephem-4-carboxylic acid (a) To a solution of 400mg of 7β-bromoacetamido-7α-methoxy-3-(1-methyl-1H-tetrazol-5-yl)thiomethyl-3-cephem-4-carboxylic acid in 3ml of dimethylformamide was added 252mg of triethylamine under stirring and ice-cooling, and subsequently 0.5ml of a solution of 88.4mg of mercaptopropionic acid in dimethylformamide. The reaction temperature was raised to the room temperature, the mixture was stirred for 3 hours, and the substance precipitated was removed by filtration. The filtrate was concentrated to dryness under reduced pressure, and the residue was dissolved in acetone and purified using three preparative thin layer chromatography plates (solvent system, n-butanol:acetic acid:water = 4:1:1) to give 150mg of 7β-(2-carboxyethylthioacetamido)-7α-methoxy-3-(1-methyl-1H-tetrazol-5-yl)thiomethyl-3-cephem-4-carboxylic acid (Rf: 0.31). Ninety milligrams of the above product was purified again by thin layer chromatography (solvent system, chloroform:methanol:water = 6:4:1) affording 50mg of a pure substance.

NMR spectrum δ ppm (deuterioaceton)
2.65–2.90 (4H, multiplet, HOOCCH$_2$CH$_2$S-)
3.40 (2H, singlet, -SCH$_2$CONH-)
3.50 (3H, singlet, OCH$_3$ at 7-position)
3.65 (2H, doublet, H$_2$ at 2-position)
3.95 (3H, singlet, N-CH$_3$)
4.40 (2H, doublet, -CH$_2$S- at 3-position)
5.02 (1H, singlet, H at 6-position)

(b)-1 To 15ml of a methanol solution containing 208.5 mg of metallic sodium was added a solution of 3.0g of [2-(diphenylmethoxycarbonyl)ethyl]thioacetic acid in 6ml of methanol at −10° C. After stirring at −5–0° C. for 30 minutes, the mixture was poured into ethanol (about 20 times volume of the methanol). The precipitated sodium [2-diphenylmethoxycarbonyl)ethyl]thioacetate was collected on a filter, washed with ether and dried. The yield was 2.58g (80.3%). To 40ml of dichloromethane suspension of 3.99g of sodium [2-(diphenylmethoxycarbonyl) ethyl]thioacetate were added 2.9ml of oxalyl chloride and 2 drops of dimethylformamide under ice-cooling and stirring. The mixture foamed intensely. After stirring under ice-cooling for one hour, the mixture was concentrated under reduced pressure to give 3.55g of [2-(diphenylmethoxycarbonyl)ethyl]thioacetyl chloride as a yellow syrup. To 50ml of dichloroethane solution containing 2.0g of benzhydryl 7β-amino-7α-methoxy-3-(1-methyl-1H-tetrazol-5-yl)thiomethyl-3-cephem-4-carboxylate were added 1.52g of diethyl aniline and 30ml of dichloroethane solution containing [2-(diphenylmethoxycarbonyl)ethyl]thioacetyl chloride (2.7 times equivalent mole) at −20° C. under stirring. The mixture was stirred at −10–−5° C. for one hour. After addition of ethyl acetate, the mixture was washed successively with an aqueous potassium bisulfate (×2), an aqueous sodium bicarbonate (×2) and a saturated aqueous sodium chloride (×1) and dried over magnesium sulfate. The solvent was distilled off under reduced pressure and the residue was purified by silica gel dry column (developing solvent; benzene:ethyl acetate = 3:1) to give 2.4g of benzhydryl 7β--{[2-diphenylmethoxycarbonyl)ethyl]thioacetamido}-7α-methoxy-3-(1-methyl-1H-tetrazol-5-yl)thiomethyl-3-cephem-4-carboxylate as brown syrup (yield 75.0%).

To 16ml of anisole solution containing 1.51g of benzhydryl 7β-{[2-(diphenylmethoxycarbonyl)ethyl]thioacetamido}-7α-methoxy-3-(1-methyl-1H-tetrazol-5-yl)-thiomethyl-3-cephem-4-carboxylate was added 8ml of trifluoroacetic acid at −15° C., followed by stirring at 0° C. for 1 hour. The solvent was distilled off and ethyl acetate was added to the residue. The mixture was extracted three times with 10% aqueous dipotassium hydrogen phosphate solution. The extract was washed with ethyl acetate, adjusted to pH 2.0 by 3N-HCl and extracted four times with ethyl acetate. The extract was washed with water, dried over magnesium sulfate and concentrated to dryness under reduced pressure. The residue was added to ether to give 600mg of the desired product as a pale yellow powder (yield 66.0%). The nuclear magnetic resonance spectrum of the product thus obtained agreed with that of the product obtained in the above (a).

(b)-2 To an ice-cold suspension of 2g of 7β-amino-7α-methoxy-3-(1-methyl-1H-tetrazol-5-yl)thiomethyl-3-cephem-4-carboxylic acid trimethyl-benzyl ammonium salt in 30ml of dichloroethane was added 1.6g of diethylaniline and 30ml of dichloroethane solution containing 3.5g of crude [2-(diphenylmethoxycarbonyl)ethyl]thioacetyl chloride with stirring. The mixture was stirred for one hour. Then the reaction mixture was extracted with 10% dipotassium hydrogen phosphate. The extract was washed with ethyl acetate and then adjusted to pH 2 with 3N-HCl and extracted with ethyl acetate. The extract was concentrated to dryness under reduced pressure to give 1g of 7β-{[2-(diphenylmethoxycarbonyl)ethyl]thioacetamido}-7α-methoxy-3-(1-methyl-1H-tetrazol-5-yl)thiomethyl-3-cephem-4-carboxylic acid. By the same procedure to the above (b), diphenylmethyl group was removed to give the desired product. The infrared absorption spectrum and the nuclear magnetic resonance spectrum of the desired product thus obtained agreed with those of the product obtained in the above (b).

(c) To 10ml of phosphate buffer solution (pH 7.0) were added 300mg of 7β-[(2-carboxyethyl)thioacetamido]-7α-methoxycephalosporanic acid, 200mg of 5-mercapto-1-methyl-1H-tetrazole and 100mg of sodium hydrogen carbonate. The mixture was stirred at 65°–70° C. in water bath for 4–5 hours. The mixture was adjusted to pH 5.5 by addition of 10% hydrochloric acid, washed twice with ethyl acetate, adjusted to pH 2.0 and extracted with ethyl acetate. The extract was dried and concentrated under reduced pressure to dryness to give 100mg of 7β-[(2-carboxyethyl)thioacetamido]-7α-methoxy-3-(1-methyl-1H-tetrazol-5-yl)thiomethyl-3-cephem-4-carboxylic acid as a pale yellow powder.

The infrared absorption spectrum and the nuclear magnetic resonance spectrum of the product thus obtained agreed with those of the product obtained in the above method (b).

EXAMPLE 2

7α-Methoxy-7β-trifluoromethylthioacetamido-3-(1-methyl-1H-tetrazol-5-yl)thiomethyl-3-cephem-4-carboxylic Acid (a) To a solution of 400mg of 7β-bromoacetamido-7α-methoxy-3-(1-methyl-1H-tetrazol-5-yl)thiomethyl-3-cephem-4-carboxylic acid in 3ml of dimethylformamide was added 160mg of triethylamine and subsequently 200 mg of silver salt of trifluoromethylmercaptan under stirring and ice-cooling. After stirring for 3 hours at room temperature, an insoluble substance was removed by filtration and the filtrate was concentrated to dryness under reduced pressure. To the residue were added ethyl acetate and a 10% aqueous solution of dipotassium hydrogen phosphate. After stirring the mixture, the aqueous layer was separated, washed with ethyl acetate, adjusted to pH 2 by an addition of 10% hydrochloric acid and extracted with ethyl acetate. The extract was concentrated to dryness, the residue was dissolved in acetone and purified by silica gel preparatory thin layer chromatography (20 × 20cm) using a solvent system (n-butanol:acetic acid:water = 4:1:1) affording 110mg of 7α-methoxy-7β-trifluoromethyl-thioacetamido-3-(1-methyl-1H-tetrazol-5-yl)thiomethyl-3-cephem-4-carboxylic acid as a light yellow powder.

NMR spectrum δ ppm (deuterioacetone)
3.56 (3H, singlet, OCH$_3$ at 7-position)
3.59 (2H, doublet, H$_2$ at 2-position)
3.80 (2H, singlet, CF$_3$SCH$_2$)
3.95 (3H, singlet, n - CH$_3$)
4.35 (2H, quartet, CH$_2$S at 3-position)
5.10 (1H, singlet, H at 6-position)

A solution of 600mg of benzhydryl 7β-amino-7α-methoxy-3-(1-methyl-1H-tetrazol-5-yl)thiomethyl-3-cephem-4-carboxylate in 50ml of methylene chloride was chilled to below 0° C. by means of a freezing mixture, to which 365mg of N,N-diethylaniline and subsequently a solution of 370mg of trifluoromethylthioacetyl chloride in 10ml of methylene chloride were added, and the mixture was agitated for 30 minutes. The reaction mixture was diluted with a suitable amount of ethyl acetate, washed successively with an aqueous potassium hydrogen sulfate solution, an aqueous sodium hydrogen carbonate solution and finally with water, dried over anhydrous magnesium sulfate, and the solvent was removed from the mixture affording benzhydryl 7α-methoxy-7β-trifluoromethylthioacetamido-3-(1-methyl-1H-tetrazol-5-yl)thiomethyl-3-cephem-4-carboxylate as an oily substance. The oily substance thus obtained was purified with two preparative thin layer chromatography plates (20 × 20 × 0.2cm) using a mixture of benzene:ethyl acetate (2:1) as developing solvent to give 150mg of the product.

NMR spectrum δ ppm (deuteriochloroform)
3.55 (3H, singlet, OCH$_3$ at 7-position)
3.60 (2H, doublet, H$_2$ at 2-position)
3.70 (2H, singlet, CF$_3$SCH$_2$)
3.80 (3H, singlet, N-CH$_3$)
4.30 (2H, quartet, -CH$_2$S at 3-position)
5.01 (1H, singlet, H at 6-position)
6.90 (1H, singlet, COOCH(C$_6$H$_5$)$_2$)
7.31 (10H, singlet, two C$_6$H$_5$ groups)

To a solution of 150mg of benzhydryl 7α-methoxy-7β-trifluoromethylthioacetamido-3-(1-methyl-1H-tetrazol-5-yl)thiomethyl-3-cephem-4-carboxylate prepared by the above process in 2ml of anisole was added 1ml of trifluoroacetic acid under stirring and ice-cooling. After stirring for 30 minutes under ice-cooling, nearly all the solvent was removed under reduced pressure from the reaction mixture, the residue dissolved in ethyl acetate, the solution extracted with 10% aqueous dipotassium hydrogen phosphate solution. The extract was washed with ethyl acetate, adjusted to pH 2 by an addition of aqueous potassium hydrogen sulfate solution, and the precipitated carboxylic acid was extracted with ethyl acetate. The extract was dried over anhydrous magnesium sulfate and the solvent was removed to give 40mg of 7α-methoxy-7β-trifluoromethylthioacetamido-3-(1-methyl-1H-tetrazol-5-yl)thiomethyl-3-cephem-4-carboxylic acid as an amorphous powder.

NMR spectrum δ ppm (deuterioacetone)
3.56 (3H, singlet, OCH$_3$ at 7-position)
3.59 (2H, doublet, H$_2$ at 2-position)
3.80 (2H, singlet, CF$_3$SCH$_2$)
3.95 (3H, singlet, N-CH$_3$)
4.35 (2H, quartet, CH$_2$S- at 3-position)
5.10 (1H, singlet, H at 6-position)

(c) To 10ml of phosphate buffer solution (pH 7.0) were added 300mg of 3-acetoxymethyl-7α-methoxy-7β-[(trifluoromethyl)thioacetamido]-3-cephem-4-carboxylic acid, 200mg of 5-mercapto-1-methyl-1H-tetrazolyl and 100mg of sodium bicarbonate. The mixture was stirred at 65°–70° C. in water bath for 4–5 hours. The mixture was adjusted to pH 5.5 by addition of 10% hydrochloric acid, washed twice with ethyl acetate, adjusted to pH 2.0 and extracted with ethyl acetate. The extract was dried and concentrated to dryness under reduced pressure to give 70mg of the desired product as pale yellow powder.

NMR spectrum δ ppm (deuterioacetone)
3.52 (3H, singlet, OCH$_3$ at 7-position)
3.71 (2H, doublet, H$_2$ at 2-position)
4.01 (3H, singlet, N-CH$_3$)
4.04 (2H, singlet, CF$_3$SCH$_2$)
4.43 (2H, quartet, CH$_2$S at 3-position)
5.10 (1H, singlet, H at 6-position)

What is claimed is:
1. A 7-methoxycephalosporin having the formula

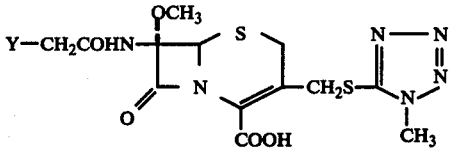

wherein Y is a 2-carboxyethylthio group and a nontoxic pharmaceutically acceptable salt thereof.

2. 7β-(2-Carboxyethylthioacetamido)-7α-methoxy-3-(1-methyl-1H-tetrazol-5-yl)-thiomethyl-3-cephem-4-carboxylic acid of the formula of claim 1.

3. A salt of said 7-methoxycephalosporin of claim 1 selected from the group consisting of an alkali metal salt, an alkaline earth metal salt, an aluminum salt, an ammonium salt and a substituted ammonium salt.

* * * * *